United States Patent [19]

Kanda et al.

[11] Patent Number: 5,028,675
[45] Date of Patent: Jul. 2, 1991

[54] POLYAMIDE RESIN AND METHOD FOR PREPARATION OF REAGENTS FOR IMMUNODIAGNOSTIC USE

[75] Inventors: Patrick Kanda; Ronald C. Kennedy, both of San Antonio; James T. Sparrow, Houston, all of Tex.

[73] Assignees: Southwest Foundation for Biomedical Research, San Antonio; Baylor College of Medicine, Houston, both of Tex.

[21] Appl. No.: 309,914

[22] Filed: Feb. 10, 1989

Related U.S. Application Data

[63] Continuation of Ser. No. 858,216, Apr. 30, 1986, abandoned.

[51] Int. Cl.$^5$ ................................................ C08F 4/30
[52] U.S. Cl. .................................... 526/229; 526/288; 526/307.3
[58] Field of Search .................... 526/310, 303.1, 208, 526/288, 306, 307

[56] References Cited

U.S. PATENT DOCUMENTS

| | | | |
|---|---|---|---|
| 2,576,502 | 11/1951 | Dalton | 526/306 |
| 2,656,339 | 10/1953 | Padbury | 526/84 |
| 2,893,970 | 7/1959 | Caldwell et al. | 526/306 |
| 3,032,539 | 5/1962 | Schuller et al. | 526/310 |
| 3,057,833 | 10/1962 | Devlin | 526/310 |
| 3,061,595 | 10/1962 | Dorion et al. | 526/306 |
| 3,062,798 | 11/1962 | Lovett | 526/310 |
| 3,912,607 | 10/1975 | Communal et al. | 522/175 |
| 3,925,267 | 12/1975 | Coupek et al. | 526/306 |
| 4,074,039 | 2/1978 | Lim et al. | 526/306 |
| 4,138,539 | 2/1979 | Landolt et al. | 526/93 |
| 4,172,066 | 10/1979 | Zweigle et al. | 526/306 |
| 4,504,640 | 3/1985 | Harada et al. | 526/310 |
| 4,528,348 | 7/1985 | Turner et al. | 526/303.1 |
| 4,658,000 | 4/1989 | Tyihak et al. | 526/303.1 |
| 4,812,540 | 3/1989 | Kageno et al. | 526/310 |

FOREIGN PATENT DOCUMENTS

| | | | |
|---|---|---|---|
| 0095233 | 11/1983 | European Pat. Off. | 526/310 |
| 2123013 | 1/1984 | United Kingdom | 526/303.1 |
| 2134531 | 8/1984 | United Kingdom | 526/307.3 |

OTHER PUBLICATIONS

"The Synthesis of Ribonuclease A", Gutte, Bernd and R. B. Merrifield, *The Journal of Biological Chemistry*, vol. 246, No. 6, Mar. 25, 1971, pp. 1929–1941.

*The Peptides: Analysis, Synthesis, Biology*, vol. 2 "Special Methods in Peptide Synthesis, Part A", ed. Gross, Erhard & Johannes Meinehofer, Academic Press: NY 1980, pp. 21–24.

*Primary Examiner*—Joseph L. Schofer
*Assistant Examiner*—N. Sarofim
*Attorney, Agent, or Firm*—Cox & Smith

[57] ABSTRACT

A polyamide resin for use in peptide and protein synthesis, and a method of preparing and using same. The polyamide resin is prepared by cross-linking a dimethylacrylamide monomer by co-polymerization with a functional monomer in an aqueous solution, emulsifying the aqueous solution in an organic solvent and isolating the polyamide resin beads formed by adding an initiator and a promoter. The beads are used as a solid phase for peptide and protein synthesis according to methods known in the art. The conjugate of the polyamide resin and the synthesized peptide or protein is used directly for immunoassays or immunization without the need for separation of the peptide or protein from the resin and subsequent purification.

13 Claims, 1 Drawing Sheet

POLYAMIDE RESIN AND METHOD FOR PREPARATION OF REAGENTS FOR IMMUNODIAGNOSTIC USE

STATEMENT REGARDING GOVERNMENT SUPPORT

This invention was made with Government support under one or more of the following NIH grants: 2 RO, HL 30064-03; HL 27341-03; HL 17269. The Government has certain rights in this invention.

This application is a continuation of co-pending application Ser. No. 858,216, filed Apr. 30, 1986 now abandoned.

BACKGROUND OF THE INVENTION

The present invention relates to the synthesis and use of synthetic peptides and proteins to induce an immune response in experimental animals. More particularly, the present invention relates to a polyamide resin, a method of making that polyamide resin, a method of inducing an immune response in an experimental animal using a conjugate of a peptide or protein synthesized on that resin, and the the use of the resin for immunodiagnostic purposes.

Solid phase peptide synthesis is a valuable tool for investigating the structure and mechanism of action of proteins. Most such synthetic methods involve the use of a cross-linked polystyrene based resin as the solid phase to which the peptide is anchored during assembly, usually through a linker molecule. Assembly is accomplished by a repetitive cycle of adding a protected amino acid to the solid phase, selectively removing (deprotecting) a protective group on that amino acid, and adding additional suitably protected amino acids (for a review, see Merrifield, R.B., "Solid-phase Peptide Synthesis", 32 Adv. Enzymology 221 (1969)).

Although cross-linked, polystyrene based resins are most commonly used as supports in solid phase peptide synthesis, their relatively hydrophobic character in comparison to the polar organic media required to solubilize reactants can be problematic in peptide chain assembly. Such media may freely solvate the growing peptide, yet incompletely swell the polystyrene matrix. Within the polymer lattice, impaired diffusion of reagents and steric hindrance can contribute to lowered efficiency during coupling cycles, which, on a repeated basis, lowers final yields appreciably. During the early stages of assembly, when the resin to peptide mass ratio is high and the physical properties of the support dominate, this lowered efficiency is particularly acute.

Those shortcomings led to the development of a cross-linked, polydimethylacrylamide based support which is highly polar in character and is freely permeated by the requisite solvents for peptide synthesis. Atherton, E., D.L.J. Clive and R.C. Sheppard, "Polyamide Supports For Polypeptide Synthesis", 97 J. Amer. Chem. Soc. 6584 (1975); Arshady, R., E. Atherton, M.J. Gait, K. Lee and R.C. Sheppard, "Easily Prepared Polar Support For Solid Phase Peptide And Oligonucleotide Synthesis". 1979 J.C.S. Chem. Comm. 425 (1979). The polyamide resin, as the amino methyl derivative, can accommodate synthetic schemes incorporating alternate protection strategies through selection of the appropriate linker molecule, which links the C-terminal residue to the support. The peptide or protein thus synthesized, which will be referred to throughout the present disclosure as a "protide", can be used in a number of investigative applications.

Of particular interest to the present invention is the use of the protide as an immunogen. It has previously been demonstrated that synthetic peptides analogous to sequences contained in viral encoded proteins have proven useful for identification of native antigen determinants associated with such proteins. Several laboratories have reported studies on the antigenic activity of various HBsAg synthetic peptides. Dreesman, G.R., et al., 295 Nature 158 (1982); Lerner, R.A., et al. 78 Proc. Natl. Acad. Sci. USA 3403 (1981); Prince, A.M., et al., 79 Proc. Natl. Acad. Sci. USA 579 (1982). The induction of an antibody response to HBsAg, using such peptides, proved to be relatively weak, but could be enhanced through coupling of peptides to a carrier protein prior to immunization. Lerner, et al., supra; Sanchez, Y., et al., 18 Intervirology 209 (1982). Because the prediction of potential antigenic determinants of immunogenic proteins based on primary sequences analysis is not exact, the identification of putative epitopes through trial and error can be laborious. A method which involves the delineation of native antigenic sequences with synthetic peptides which does not require purification of the synthetic peptide and coupling of the peptide to carrier proteins offers significant advantages. It is, therefore, an object of the present invention to provide a method of preparing a polyamide resin upon which a protide can be synthesized using solid phase synthetic methods which can be injected into an experimental animal to induce an immunogenic response without separation of the protide from the resin.

It is another object of the present invention to provide a polyamide resin for solid phase protide synthesis, and a conjugate of that polyamide resin and synthesized protide, which can be injected into an experimental animal to induce an immunogenic response.

It is another object of the present invention to provide a polyamide resin-protide conjugate for use in in vitro immunological assays.

Another object of the present invention is to provide a method of preparing a polyamide resin for solid phase protide synthesis comprising cross-linking a dimethylacrylamide monomer with a molecule containing a functional group by free radical co-polymerization in an aqueous solution which has been emulsified by a detergent when added to an organic solvent medium.

Another object of the present invention is to provide a method of inducing an immunogenic response in an experimental animal with a synthetic peptide or protein comprising preparing a polyamide resin, synthesizing a peptide or protein on that polyamide resin, and immunizing an experimental animal with the polyamide resin-synthetic peptide or synthetic protein conjugate.

Another object of the present invention is to provide an assay for detection of proteins such as antigens and antibodies using the polyamide resin-protide conjugate of the present invention.

Another object of the present invention is to provide a method of inducing an immunogenic response in an experimental animal using the polyamide resin-protide conjugate of the present invention.

Another object of the present invention is to provide a polyamide resin for solid phase protide synthesis which does not require the separation of the protide from the resin and the subsequent purification of the protide before the use of that protide to, for instance, induce an immunogenic response.

Another object of the present invention is to provide a polyamide resin for solid phase protide synthesis which is particularly useful in the mapping of the antigenic determinants of a protein as a result of the elimination of the steps of separation of the protide from the resin and the subsequent purification of the protide before the use of the protide in a binding assay.

These and other objects and advantages of the present invention will be clear to those skilled in the art from the following description.

SUMMARY OF THE INVENTION

These objects are accomplished by providing a method of preparing a polyamide resin for solid phase protide synthesis comprising cross-linking a dimethylacrylamide monomer with a molecule containing a functional group in a free radical reaction with an initiator and a promotor. The beaded polyamide resin is then polymerized in the emulsion formed when an aqueous solution of those reagents is suspended in an organic medium. The beads are then isolated and used as the solid phase for synthesis of a protide.

Also provided is a method of inducing an immunogenic response in an experimental animal comprising preparing a polyamide resin, synthesizing a protide on the polyamide resin, and immunizing an experimental animal with the polyamide resin-protide conjugate.

An in vitro diagnostic assay is also provided which comprises preparing a polyamide resin, synthesizing a protide on the resin to form a polyamide resin-protide conjugate, and contacting the polyamide resin-protide conjugate with a body fluid suspected of containing antibodies capable of binding specifically to the protide. The bound antibodies are then detected using, for instance, an enzyme linked immunosorbent assay.

DETAILED DESCRIPTION OF THE INVENTION

Figure 1:
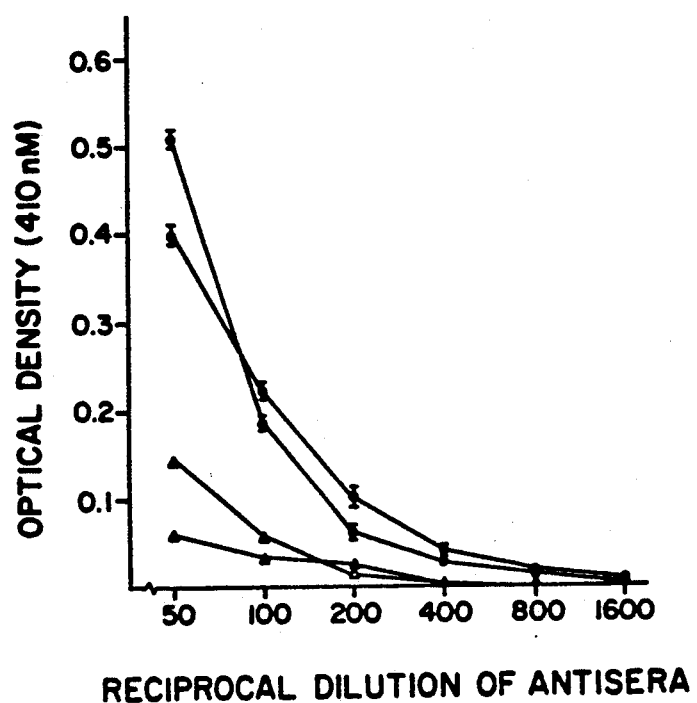
FIG. 1 is a graph of optical density at 410 nm as a function of the reciprocal dilution of rabbit antisera to the polyamide resin-HTLV-III peptide 503–532 conjugate obtained by enzyme linked immunosorbent assay. The circles represent data from rabbits immunized with that conjugate, the triangles represent data from those same rabbits before immunization.

As noted above, the term "protide", as used herein, refers to both the peptides and proteins which are synthesized according to the method of the present invention. A significant advantage of the method of the present invention is that the protide synthesized on the polyamide resin can be used to induce an immunogenic response in a mammal without being separated from the resin and purified.

The usual method of coupling the protide to polystyrene based resins is through a benzyl ester derivative, and separation of the protide from the resin is usually accomplished by either acidic or basic cleavage. Benzyl esters are susceptible to several such methods of cleavage, but are also stable throughout the multiple deprotection, neutralization and coupling reactions which are characteristic of solid phase synthetic methods. Hydrazine has also been used to separate the protide from the resin (Kessler, W. and B. Iselin, 49 Helv. Chim. Acta 1330 (1966)) as have various ammonolytic (Manning, M., 90 J.Am.Chem.Soc. 1348 (1968)) and other methods. However, those methods all require that appropriate steps be taken to avoid damage to the protide followed by purification of the protide from the by-products of the synthesis, including amino acids, short peptides, decomposition products of the resin, and sometimes, peptides containing incompletely removed protecting groups. Although purification can sometimes be accomplished by a direct crystallization, in syntheses in which the contaminating peptides are of approximately the same size and composition as the desired product, more selective techniques must be employed. Regardless of the method of separation and purification, those requirements add time-consuming steps to the synthesis which often lower the total yield of protide. The method of the present invention requires no such separation and purification, thereby decreasing the amount of time required to accomplish the synthesis and raising the protide yield.

The polyamide resin of the present invention is prepared by cross-linking a commercially available dimethylacrylamide monomer in aqueous solution using a diaminoalkane, preferably a diaminoalkane having alkenoyl groups at either end of the molecule such as N,N'-bis-alkenoyl-diaminoalkane. In a presently preferred embodiment, the cross-linker is either N,N'-bisacrylyl-1,3-diaminopropane or N,N'-bisacrylyl-1,3-diaminobutane prepared according to the method of Halpern and Sparrow (J.A. Halpern and J.T. Sparrow, "An Improved Procedure For The Synthesis Of N,N'-bisacrylyldiaminoalkanes", 10 Synthetic Comm. 569 (1980)), hereby incorporated in its totality by this specific reference thereto. The use of the propane analog is preferred because it yields a polymer of larger pore size and improved swelling properties during protide synthesis than the polymer obtained by use of the ethyl analog. However, it will be understood by those skilled in the art who have the benefit of this disclosure that the other diaminoalkanes listed in that report, N,N'-bisacrylyl-1,2 diaminoethane and N,N'-bisacrylyl-1,6-diaminohexane, as well as other diaminoalkanes, are also appropriate for use in the preparation of the resin of the present invention.

A functional monomer is included in the cross-linked resin of the present invention. The term "functional monomer" refers to those alkenyl amines which are used to anchor the C-terminal amino acid of a synthetic protide to the resin. The functional monomer, when protected with the methylsulfonylethyloxycarbonyl (MSC) group (see Tesser, G.I. and I.C. Balvert-Geers, "The Methylsulfonylethyloxycarbonyl Group, A New And Versatile Amino Protective Function", 7 Int. J. Peptide Protein Res. 295 (1975)), is referred to as an MSC alkenyl amine. Those functional monomers are prepared by reaction of the commercially available chloride derivative with the alkenylamine, and the MSC protective group is subsequently removed with base. However, the MSC group is not required. The polyamide resin of the present invention is also prepared by simply adding an excess of the allylamine, followed by filtering or other method to remove the resulting fines. The amount of functional monomer added is selected to yield a resin substitution of between about 0.1 mmol and about 0.5 mmol per gram of resin, and preferably in the range of about 0.2 mmol to about 0.4 mmol per gram of resin. The initiator can be any of the initiators known to those skilled in the art such as a persulfate or riboflavin, and is preferably ammonium persulfate.

Because the above-described substances are combined in aqueous solution, they are collectively referred to as "the aqueous phase'. The next step in the preparation of the polyamide resin of the present invention is to combine the aqueous phase with an organic phase. The term "organic phase" refers to an organic solvent which, when combined with the aqueous phase and stirred, results in a suspension from which the resin of the present invention is obtained. In a presently preferred embodiment, the organic phase comprises a mixture of hexane and carbon tetrachloride.

An emulsifier is added during the stirring to allow for the formation of beads of uniform size. The emulsifier can be any detergent known to those skilled in the art, and in a presently preferred embodiment, is either sorbitan sesquioleate, sorbitan monolaurate or sorbitan monodecanoate. The amount of detergent added is adjusted to give a spherical resin of approximately uniform size. A decrease in the amount of detergent results in an emulsion which yields increased amounts of larger, amorphous material, which could contribute to a reduction to the internal growing chains of amino acids. An increase in the amount of detergent increases the amount of fine material, which is difficult to remove the loss of significant amounts of the resin. Those fin clog the reaction vessels of the peptide synthesizer as well as associated lines and valves.

A promoter is then added to promote the polymerization of the monomers in the suspension, resulting in the formation of beads of the polyamide resin of the present invention. A number of promotors are known to those skilled in the art, but particular success in preparing the polyamide resin of the present invention has been obtained with N,N,N',N'-tetramethylethylenediamine (TEMED). The resulting beads are then filtered and washed, the MSC group (if present) is removed with base, and the beads are dried. The beads may then be sifted through a mesh sieve to insure relatively uniform size. Overall yields using the method of the present invention ranged from about 87% to about 94% from starting monomers.

The aminomethyl, cross-linked polydimethylacrylamide resin of the present invention provides maximum exposure of the protide in an aqueous solution and the resin-polymer backbone does not restrict the protide conformationally. The exposure of the protide is the result of the ability of the polyamide resin to swell to many times it dry bed volume when highly solvated by water.

Protides are then on the beads by coupling to a linker which is at to the resin with an activator. The term "linker" refers linking group which links the carboxyl group of the first acid of the protide to the polymeric resin. In the preferred embodiment, this linker is an oxyalkyl benzoic acid (OBA) to which an amino acid residue is coupled to serve as the first amino acid in the protide chain. Because the OBA linker is used to attach the C-terminal amino acid to the polyamide resin of the present invention, anhydrous hydrogen fluoride can be used to remove the side chain protecting groups from the protide without significant loss of the protide from the resin. In the below-described examples, the amino acid of choice is glycine, which is protected with the t-butyloxycarbonyl (t-Boc) protecting group, but it will be understood by those skilled in the art who have the benefit of this disclosure that the amino acid could be any amino acid, particularly, the amino acid which is the first amino acid in the protide to be synthesized, and that other protecting groups are equally suitable. The glycine residue serves the additional function of a spacer between the protide and the resin-polymer backbone.

The Boc-glycyl-4-(oxymethyl) benzoic acid which is the presently preferred linker was prepared by a modification of the method described by Mitchell, et al. (Mitchell, A.R., S.B.H. Kent, M. Engelhard and R.B. Merrifield, A new synthetic route to tert-butyloxycarbonylaminoacyl-4-(oxymethyl) phenylacetamidomethyl-resin, an improved support of solid-phase peptide synthesis, 43 J. Org. Chem. 2845 (1978), which is incorporated herein in its totality by this specific reference thereto. An important modification of the Mitchell, et al., method is the elimination of the use of dimethylformamide as a solvent. That solvent is difficult to evaporate, consequently, even though evaporation can be hastened by raising the temperature, the method is still time-consuming. The activator used to couple the linker to the polyamide resin prepared as described above is diisopropyl carbodiimide and 4-dimethylaminopyridine, but it will be understood by those skilled in the art that other activators such as dicyclohexylcarbodiimide and 4-methylpyrrolindinopyridine are equally suitable for such a purpose.

After synthesis of the protide on the polyamide resin, the polyamide resin-protide conjugate is used for a number of purposes, including in vitro assays, inducing an immunogenic response in experimental animals, or mapping antigenic determinants. For instance, an in vitro assay is conducted by crushing the beaded polyamide resin-protide conjugate with a mortar and a pestle and absorbing the crushed conjugate onto a solid phase such as a microtiter test plate with neutral pH buffer. Serum or other body fluid suspected of containing an antibody capable of specifically binding the protein or peptide on the resin is then incubated with the absorbed conjugate, unbound antibodies are removed by washing, and the bound antibodies are detected by enzyme linked immunosorbent assay, biotin-avidin amplified assay or other detection methods such as are known in the art.

The polyamide resin-protide conjugate can also be used to map antigenic determinants by simply removing a portion of the polyamide resin-protide conjugate at intervals during the synthesis of the protide, deprotecting the protide, and testing each removed portion in serial fashion to determine that point in the synthesis at which the protide binds antibody. This method is made possible by the elimination of the separation and purification steps required in other synthetic methods. The conjugate can also be tested for its ability to bind antibody by crushing and absorbing to a solid support such as a microtiter test plate and assayed as described above. Separation of the protide from the resin and purification of the protide is not required for such an assay.

The polyamide resin-protide conjugate is also useful as an immunogen. The conjugate is used directly for immunization of experimental animals with or without an adjuvant. The term "experimental animal", as used herein, refers to any animal capable of an immune response. The experimental animals of primary interest are mammals, but an immunogenic response can be induced in other experimental animals such as birds using the method of the present invention. For instance, an immune response specific for hepatitis B, as measured by radioimmunoassay, was induced by immunization of rabbits using a conjugate comprised of a synthetic peptide with the same sequence as the hepatitis B antigen (HBsAG) peptide 119-159 emulsified in Freund's complete adjuvant. Similar results, as measured by radioimmunoprecipitation, were obtained with a conjugate comprising a peptide corresponding to the protein coat of the AIDS virus HTLV-III and the polyamide resin of the present invention.

The present invention can be better understood by reference to the following examples, which are presented for purposes of exemplification and not limitation.

EXAMPLE I

Preparation of Functional Monomer

Five grams of (26.8 mmol) 2-methylsulfonyl ethyloxycarbonyl chloride (MSC chloride) (K+K Labs, ICN) were dissolved in 15 ml acetonitrile and added dropwise over a 20 minute period to a stirred solution of 2.1 ml (28 mmol) redistilled allylamine (Kodak) and 4.9 ml (28 mmol) redistilled diisopropylethylamine (DIEA) in 20 ml acetonitrile. (DIEA (Aldrich) was refluxed over ninhydrin and redistilled.) The solution was stirred an additional two hours and the solvent evaporated. The residue was taken up in 250 ml ethyl acetate and allowed to stand for one-two hours. The bulk of the DIEA hydrochloride salt precipitated as needles. After filtration and evaporation, the crude material was dissolved in a minimal amount of chloroform and loaded onto a silica gel G-60 column (60 g) packed in the same solvent. Elution with chloroform yielded pure MSC-allylamine. ($R_F$ on TLC=0.64 (Solvent=$CHCl_3$:$CH_3OH$, 9:1).)

The remaining DIEA salts adsorbed to the column under these conditions. Occasionally, material migrating near the solvent front on TLC contaminated the MSC-allylamine column fractions. That material was removed by crystallizing the MSC allylamine from methylene chloride-hexane at $-20°$ C. Yield was 4.8 g (86% from MSC chloride).

EXAMPLE II

Preparation of Cross-Linker

The cross-linker N,N'-bisacrylyl-1,3-diaminopropane was prepared according to the method set out in Helpern and Sparrow, supra. Briefly, diaminopropane (Aldrich) was dissolved in acetonitrile and added dropwise to an acrylyl chloride-acetonitrile solution at $4°$ C., allowed to warm to room temperature and stirred. The diaiminopropane dihydrochloride was removed by filtration, washed with warm acetonitrile, and the combined filtrates were concentrated in vacuo. N,N'-bisacrylyl-1,3-diaminopropane was crystallized at $4°$ C. overnight and the resulting plates filtered and dried in vacuo.

EXAMPLE III

Preparation of Polyamide Resin

In a glass, 2-liter cylindrical, fluted polymerization vessel fitted with a nitrogen inlet and mechanically driven glass stirrer were added 490 ml hexane and 290 ml carbon tetrachloride. The solution was purged for 15 minutes with nitrogen to remove oxygen. To this solution was added an aqueous solution containing N,N'-bisacrylyl-1,3-diaminopropane (2.9 grams, 15.9 mmol) prepared as described in Example II mixed with 18.2 ml (175 mmol) of N,N-dimethylacrylamide (PolySciences). Ten g (48 mmol) MSC allylamine prepared as described in Example I and 120 ml water were added, and the solution was filtered and degassed before addition to the organic phase. The density of the resulting mixture was adjusted to obtain a uniform suspension with stirring at 400-450 RPM. Ammonium persulfate (BioRad) (0.5 g in 5 ml $H_2O$) and 1 ml of either sorbitan sesquioleate or sorbitan monolaurate (Sigma) were added. A solution of 3 ml N,N,N',N'-tetramethylethylenediamine (TEMED) (BioRad) in 2 ml $H_2O$, pH 6.5–7.5 (conc. HCl) was then added to the suspension. The suspended emulsion was stirred for two hours under nitrogen atmosphere. The resultant beaded material was then filtered and washed sequentially with water (one liter) methanol (one liter), a mixture of dioxane:methanol:2 N NaOH (14:5:1, two liters, to remove MSC group), water (two liters), 1 N HCl (two liters), water (two liters), and then methanol (two liters). The resin was defined by suspension in methanol and decanting ($3 \times$). After swelling in methylene chloride (Baker HPLC grade), the resin was shrunk in hexane and dried in vacuo. Large amorphous material was removed by sifting the resin through an 80 mesh (180 micron) sieve.

The degree of functionalization was checked by coupling Bocalanine to 100 mg of the resin using diisopropylcarbodiimide as activator and 4-dimethylaminopyridine (recrystallized from ethyl acetate) as catalyst. Amino acid analysis showed a substitution of 0.15 to 0.35 mmol/g resin, depending on the lot, and resins were prepared with as little as about 0.1 and as much as about 0.5 mmol/g resin depending upon the amount of allylamine added. The loaded resin gave no detectable staining with picryl-sulfonic acid, indicating the absence of unreacted free amine. When swollen in methylene chloride, the beads occupied about 2.5 times their dry bed volume. When swollen in dimethylformamide or an aqueous solution, the beads occupied approximately four and six times their dry bed volume, respectively.

EXAMPLE IV

Preparation of Linker

The linker Boc-glycyl-4-(oxymethyl) benzoic acid was prepared by modification of the method of Mitchell, et al., supra. Briefly, the 4-(bromomethyl) benzoic acid phenylacylester was prepared by dissolving 10.3 ml redistilled diisopropylethylamine and 12.05 g (60.6 mmol) bromoacetophenone in 450 ml ethyl acetate. 4-(bromomethyl) benzoic acid (13.89 g, 60.6 mmol) was added in seven equal portions over a three hour period to the stirred solution at $40°$–$50°$ C. Stirring was continued for two more hours at room temperature. Precipitated $Et_3N$ HBr was removed by filtration and the ethyl acetate solution was washed four times with 50 ml each of an aqueous solution of 10% citric acid, saturated sodium chloride, saturated sodium bicarbonate, and saturated sodium chloride. The organic phase was dried over anhydrous magnesium sulfate and freed of solvent by rotary evaporation under reduced pressure. The residue was crystallized from $CH_2Cl_2$-petroleum ether (1:3 v/v) to give the 4-(bromomethyl) benzoic acid phenylacylester.

The 4-(bromomethyl) benzoic acid phenylacylester was converted to Boc-glycyl-4-(oxymethyl) benzoic acid by dissolving Boc-L-glycine (25 mmol, 4.38g) in 15 ml methanol and titrating to neutrality with tetramethylammonium hydroxide (25% in methanol). Solvent was removed azeotropically with chloroform in vacuo, and the salt dissolved in 150 ml acetonitrile. To the stirred solution was added 5.8 g (17.5 mmol) of the 4-(bromomethyl) benzoic acid phenacyl ester prepared as described. After overnight mixing, the precipitated tetramethylammonium bromide was filtered and the solvent evaporated. The residue was dissolved in 400 ml ethyl acetate and the solution filtered. The organic phase was then washed successively with 10% aqueous citric acid (3×75 ml), 0.5 M sodium bicarbonate: 0.5 M potassium carbonate (2:1), pH 9.5 (8×75 ml), then water (3×75 ml). The solution was dried (MgSO4) and the solvent removed in vacuo. The residue was dissolved in 200 ml of 85% acetic acid to which 23 g acid washed zinc dust was added. The mixture was stirred until the phenacyl ester was no longer visible by TLC (4–5 hours). The zinc was filtered and washed with 50 ml acetic acid, and the combined solutions were lyophilized. The residue was suspended in 100 ml water:300 ml ethyl acetate, and the pH adjusted to 1.5 (conc. HCl). The aqueous layer was extracted with a second portion of ethyl acetate (200 ml), and the combined extracts were washed with water (100 ml). After drying (MgSO4) and evaporating, the Boc-glycyl-4(oxymethyl) benzoic acid was purified by recrystallization from methylene chloride:hexane at −10°. Yield was 4.5 g (14.5 mmol, 83% from the phenacyl ester).

EXAMPLE V

Coupling of Linker to Polyamide Resin

Boc-glycyl-4-(oxymethyl) benzoic acid prepared as described in Example IV was coupled to the aminomethyl polyamide resin (1.2 g) prepared as described in Example III on a Biosearch Sam II automated peptide synthesizer using diisopropylcarbodiimide and dimethylaminopyridine as activator in a 1:1 methylene chloride:dimethylformamide solution. Both methylene chloride (Baker HPLC grade) and dimethylformamide (Baker Photrex grade) were used without further purification. Following treatment with hydrogen fluoride, 50 mg of the glycyl resin was found to contain 0.13 mmol/g by amino acid analysis. Amino acid analysis was performed using a Beckman Model 119 amino acid analyzer following either a two hour hydrolysis (12 N HCl:propionic acid, 1:1, 135° C.) or 24 hour hydrolysis (6 N HCl, 110° C.) of resin bound peptides.

EXAMPLE VI

Synthesis of Hepatitis B Antigen Peptide

The hepatitis B surface antigen (HBsAg) peptide 119-159 was assembled on the aminomethyl, cross-linked polydimethylacrylamide resin prepared as described in Example III, having the Bocglycyl-4-(oxymethyl) benzoic acid linker prepared as described in Example IV attached thereto using the method described in Example V, with all residues being double coupled using a Biosearch Sam II automated peptide synthesizer. The sequence of that HBsAg peptide is as follows, and is relative to the AYW subtype:

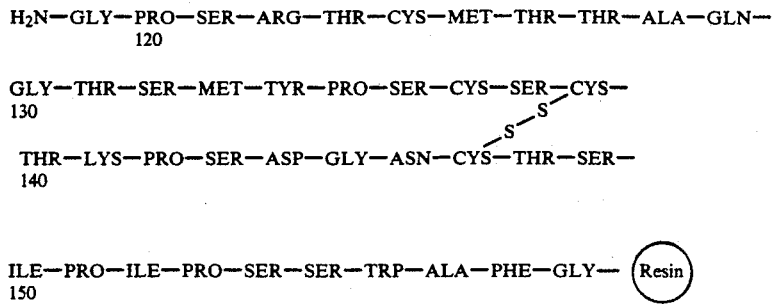

The peptide included the following substitutions to control the specific formation of disulfide loops: serine for cysteines 121, 138, and 149. The cysteines 139 and 147 sulfhydryls were blocked by the 4-methoxybenzyl group, while the sulfhydryls of cysteines at 124 and 137 were protected as the S-acetamidomethyl derivatives. α-N-tBoc protected amino acids were purchased from Bachem. Additional side chain protecting groups were as follows: formyl group for the indole nitrogen of tryptophan; benzylethers for threonine and serine hydroxyls; acetamidomethyl or 4-methoxybenzyl for cysteine sulfhydryls as described above; benzyl esters for β-carboxyl of aspartic acid and the γ-carboxyl of glutamic acid; 2-chlorobenzyloxycarbonyl for ε-amino group of lysine; 2,6-dichlorobenzyl ether for the phenolic hydroxyl of tyrosine; and the p-tosyl group for the quanidine of arginine. For the synthesis, methylene chloride (Baker HPLC grade) and DMF (Baker Photrex grade) were used without further purification. Diisopropylethylamine (DIEA) (Aldrich) was refluxed over ninhydrin and redistilled. Trifluoroacetic acid (Halocarbon) was redistilled, with the middle cut used in deblocking steps. All other chemicals were reagent grade or better and used without further purification.

Side chain protecting groups were removed from the completed peptidyl-resin by treatment with anhydrous HF (20 ml/g resin) at 0° for thirty minutes, containing 10% anisole and 2% ethanedithiol. Following evaporation of HF, the peptidyl-resin was washed successively with ether, 1% acetic acid, methanol, 5% DIEA in methylene chloride, methanol, then 1% acetic acid. The peptidyl-resin was dried in vacuo. The formyl group was removed from the tryptophan by treatment with ethanolamine at 0°. A disulfide bridge was formed between cysteines 139 and 147 by potassium ferricyanide treatment. A second disulfide bridge between cysteines 124 and 137 resulted during simultaneous removal of the acetimidomethyl moieties with a solution of iodine in acetic acid.

EXAMPLE VII

In Vitro Assay for Presence of HBsAg Antibody

Human serum can be assayed for the presence of antibody specific for the HBsAg peptide 119-159 by the following in vitro assay. A quantity of the HBsAg peptide 119-159-polyamide resin prepared as described in Example VI is crushed with a mortar and pestle. A microscope may be used to verify that the polyamide resin-peptide conjugate has been crushed. Approximately 100 μl of a solution containing between about 200 nanograms and about 10 micrograms of the crushed polyamide resin-peptide conjugate in a neutral pH buffer such as phosphate buffered saline (PBS) is absorbed to a solid phase such as Dynatech Immunolon II Microfilter test plate. Nonspecific binding sites are blocked with 10% normal goat serum (NGtS) and the plate is washed with Tween 20 PBS (T-PBS) to remove unbound antibodies.

Human sera suspected of containing antibodies specific for HBsAg peptide 119–159 and rabbit antisera produced by immunizing rabbits with the polyamide resin-HBsAg peptide 119–159 conjugate diluted in 10% NGtS is then added to the polyamide resin-peptide-coated plate and incubated for one hour at 37° C., followed by washing with T-PBS. Biotin goat anti-human IgG or biotin goat anti-rabbit IgG (Vector Laboratories, Burlingame, Calif.) is then incubated with the bound human and rabbit sera, respectively, for one hour at 37° C. The wells are washed and avidin conjugated to horseradish peroxidase (Av-HRP) is added for 20 minutes at room temperature. The wells are then washed with T-PBS to remove an unbound Av-HRP and peroxidase activity is determined using a 1 mM solution of 1,2′-azino-di(3-ethyl-benzthiazoline sulfonic acid) (Sigma Chemical Co.) and 0.03% $H_2O_2$ as substrate. The reaction is stopped with 5% (w/v) sodium dodecyl sulfate in water prior to quantitating spectrophotometrically at 410 nm using a Dynatech plate reader. Optimal dilutions of each reagent are selected by titration. All reagents for determining specific binding except the substrate are diluted in 10% NGtS.

EXAMPLE VIII

In Vitro Assay for Presence of HBsAg Antibody

Human serum was assayed for the presence of antibody to hepatitis B surface antigen by the following in vitro assay. A 10% solution of the polyamide resin-HBsAg peptide 119–159 conjugate was prepared in a buffered bovine serum albumin (BSA) solution containing a final concentration of 40% tetrahydrafuran. An equal volume of antibody specific for the HBsAg peptide 119–159 containing between 100,000 and 1,000,000 counts per minute $I^{125}$ was added and incubated with gentle rocking. The resulting suspension was centrifuged and the pellet washed with 1% BSA-Tween 20 PBS, then centrifuged again. The radioactivity of the pellet was then counted in a Gamma counter. The results clearly indicate the recognition of the polyamide resin HbsAg peptide 119-159 conjugate by native HBsAg antibody:

| | Glycyl resin (Control) | resin-HbsAg peptide 119-159 conjugate |
|---|---|---|
| IgG Human anti-HB#1 | 1240 cpm* | 22,840 |
| IgG Human anti-HB#2 | 1921 | 28,732 |
| Normal human IgG | 1432 | 1949 |

*all measurements in counts per minute

EXAMPLE IX

Use of Polyamide Resin-Protide Conjugate to Induce an Immungenic Response in Mammals The polyamide resin-peptide conjugate prepared as described in Example VI was used to induce an immunogenic response in rabbits as follows. New Zealand white female rabbits were immunized with three monthly intramuscular injections of either 200 μg HBsAg peptide 119-159 (as the peptide-resin conjugate) or only glycyl-resin emulsified in Freund's complete adjuvant (range of immunogen, 50 μg to 1 mg for rabbits). Serum was collected after bi-weekly bleeding and checked for anti-HBsAg activity using a commercially available radioimmunoassay (RIA) kit (AUSAB, Abbott Laboratories). The recognition of the native HBsAg surface antigen by the anti-peptide 119-159 antibody response induced in the rabbits is demonstrated by the following data developed by that RIA.

| RABBIT | IMMUNOGEN | IMMUNIZATION | ANTIBODY TITER[a] (RIA UNITS PER MILLILITER) |
|---|---|---|---|
| No. 1 | Glycine-Resin | Preimmune[a] | ≦8[b] |
| | | Primary | ≦8 |
| | | Secondary | ≦8 |
| | | Tertiary | ≦8 |
| No. 2 | HBsAg Peptide-Resin | Preimmune | ≦8 |
| | | Primary | ≦8 |
| | | Secondary | 183 |
| | | Tertiary | 920 |
| No. 3 | HBsAg Peptide-Resin | Preimmune | ≦8 |
| | | Primary | ≦8 |
| | | Secondary | 72 |
| | | Tertiary | 262 |

[a]Sera obtained prior to immunization.
[b]Antibody titer to HBsAg is below the sensitivity of the RIA kit and is considered not to contain specific antibodies.

As can be seen by this data, the polyamide resin-HBsAg peptide 119-159 conjugate containing a single disulfide bridge between cysteines 139 and 147, when used to immunize rabbits, yielded anti-peptide antisera which cross reacted with HBsAg.

EXAMPLE X

Synthesis of HTLV-III Antigen Peptide

The HTLV-III peptide gp 120 503-532 was assembled on the cross-linked polydimethylacrylamide resin prepared as described in Example III, having the Boc-glycyl-4-(oxymethyl) benzoic acid linker prepared as described in Example IV attached thereto using the method as described in Example V, in the same method as described for the synthesis of the HBsAG peptide 119-159 in Example VI, the only difference being the order in which the protected amino acids were added. The sequence of the HTLV-III peptide gp 120 503-532 is as follows:

gp 120 503-532

$H_2N$—VAL—PRO—THR—LYS—ALA—LYS—ARG—
503

ARG—VAL—VAL—GLN—ARG—GLU—LYS—ARG—

-continued gp 120 503-532

ALA—VAL—GLY—ILE—GLY—ALA—LEU—PHE—
LEU—GLY—PHE—LEU—GLY—ALA—GLY—
532
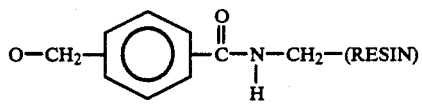
EXAMPLE XI

Use of Polyamide Resin-HTLV-III Synthetic Peptide Conjugate to Induce an Immunogenic Response Rabbits immunized with the polyamide resin-HTLV-III peptide 503–532 conjugate produced a specific anti-peptide response as determined by an enzyme linked immunosorbent assay conducted according to the method of Example VII (with the use of antisera produced by immunizing the rabbits with the polyamide resin-HTLV-III peptide 503–532 conjugate rather than the conjugate which included the HBsAg peptide 119–159 as used in that Example). The results of that immunoassay are presented graphically in FIG. 1. The data represented by the circles is data from rabbits immunized with that conjugate, the data represented by triangles is from those same rabbits before immunization (the solid circles and triangles are both from one rabbit; the open circles and triangles are both from one rabbit; the open circles and triangles are both from a second rabbit). A conjugate comprised of the polyamide resin and a third peptide failed to demonstrate significant binding. One of the rabbits produced an anti-HTLV-III response specific for the gp 120 envelope protein of HTLV-III based on a radioimmunoprecipitation assay conducted according to the method of Allan, J.S., et al. 228 Science 1091 (1985) and Barin, F., et al., 228 Science 1094 (1985), both of which are incorporated herein in their entirety by this specific reference thereto.

The ability of the rabbit antisera generated to peptide 503–532 to neutralize HTLV-III infectivity was assessed on the basis of a reduction of reverse transcriptase activity using a tenfold dilution of the HTLV-III stock with a constant amount of antisera. Barre-Sinoussi, F., et al., 220 Science 868 (1983). A single rabbit anti-peptide 503–532 antiserum efficiently reduced HTLV-III replication at day 10 compared to pooled human sera from AIDS patients at tenfold dilutions of virus. A second rabbit antiserum to that peptide failed to reduce HTLV-III replication and so was used as a control throughout the RT assay. No anti-HTLV-III activity was detected in this particular antiserum based on radioimmunoprecipitation even though the rabbit received a similar immunogen and produced a detectable anti-peptide response.

The antiserum that neutralizes HTLV-III detected both gp 120 and gp 160 envelope glycoproteins. This rabbit antiserum was found to be less efficient in neutralizing HTLV-III compared to human AIDS serum on day 12 and 15 following HTLV-III infection.

The foregoing examples are presented for purposes of exemplification of the method of the present invention. Variations in those methods will be known to those skilled in the art, and it is expected that all such variations will be made without departing from the spirit and scope of the present invention as claimed in the following claims.

We claim:

1. A method of preparing a polyamide resin, comprising:

mixing allylamine monomer with dimethylacrylamide monomer and cross-linker in an aqueous solution;

emulsifying the mixture in an organic solvent to promote the formation of polymer resin spheres of a desired size;

adding an initiator and a promoter to polymerize the allylamine monomer, dimethylacrylamide monomer and cross-linker into polyamide resin beads; and isolating the thus formed beads.

2. The method of claim 1, wherein the cross-linker comprises a diaminoalkane.

3. The method of claim 2, wherein the diaminoalkane comprises a N,N'-bisalkenoyl-diamino-alkane.

4. The method of claim 3, wherein the N,N'-bisalkenoyl-diaminoalkane is selected from the group consisting of N,N'-bisalkenoyl-1,3-diaminopropane;
N,N'-bisalkenoyl-1,3-diaminoethane;
N,N'-bisalkenoyl-1,3-diaminobutane; and
N,N'-bisalkenoyl-1,3-diaminohexane.

5. The method of claim 1, wherein the allylamine monomer carries a protective group.

6. The method of claim 5, further comprising removing the allylamine protective group from the polyamide resin by contacting the beads with a base.

7. The method of claim 1, wherein the allylamine protective group comprises methylsulfonylethyloxycarbonyl.

8. The method of claim 1, wherein the initiator comprises ammonium persulfate.

9. The method of claim 1, wherein the organic solvent comprises a mixture of hexane and carbon tetrachloride.

10. The method of claim 1, wherein the aqueous solution is emulsified with an emulsifier comprising sorbitan monolaurate, sorbitan sesquiolate of sorbitan monodecanoate.

11. The method of claim 1, wherein the promoter comprises N,N,N',N'-tetramethylethylene-diamine.

12. The method of claim 1, wherein the isolation of the beads is conducted by filtering, washing and drying.

13. A polyamide resin prepared by the method of claim 1.

* * * * *